United States Patent [19]

Pelloux-Gervais

[11] 4,314,450

[45] Feb. 9, 1982

[54] CRYOGENIC STORAGE DEVICES

[75] Inventor: Pierre Pelloux-Gervais, Grenoble, France

[73] Assignee: L'Air Liquide, Societe Anonyme pour l'Etude et l'Exploitation des Procedes Georges Claude, Paris, France

[21] Appl. No.: 184,186

[22] Filed: Sep. 4, 1980

[30] Foreign Application Priority Data

Sep. 28, 1979 [FR] France .............................. 79 24212

[51] Int. Cl.³ ............................................. F17C 7/00
[52] U.S. Cl. ......................................... 62/45; 62/78; 62/514 R
[58] Field of Search .................... 62/78, 45, 514 R

[56] References Cited

U.S. PATENT DOCUMENTS 3,187,937 6/1965 Berta .
3,195,620 7/1965 Steinhardt, Jr. ................. 62/514 R
3,707,079 12/1972 Hawker .

OTHER PUBLICATIONS

D. H. Tantam: "Developments of dewars for the storage of biological specimens," pp. 165-169, FIG. 1: Cryogenics, vol. 12, Jun. 1972, No. 3-Guildford, Surrey (GB).

Primary Examiner—Ronald C. Capossela
Attorney, Agent, or Firm—Young & Thompson

[57] ABSTRACT

The present invention relates to a device for the cryogenic storing of products. In a tank, canisters are suspended via rods, and these rods rest on the rim of the tank via retaining heads. The invention is applicable to the cryogenic storage of seeds, semen, vegetable substances, etc.

7 Claims, 4 Drawing Figures

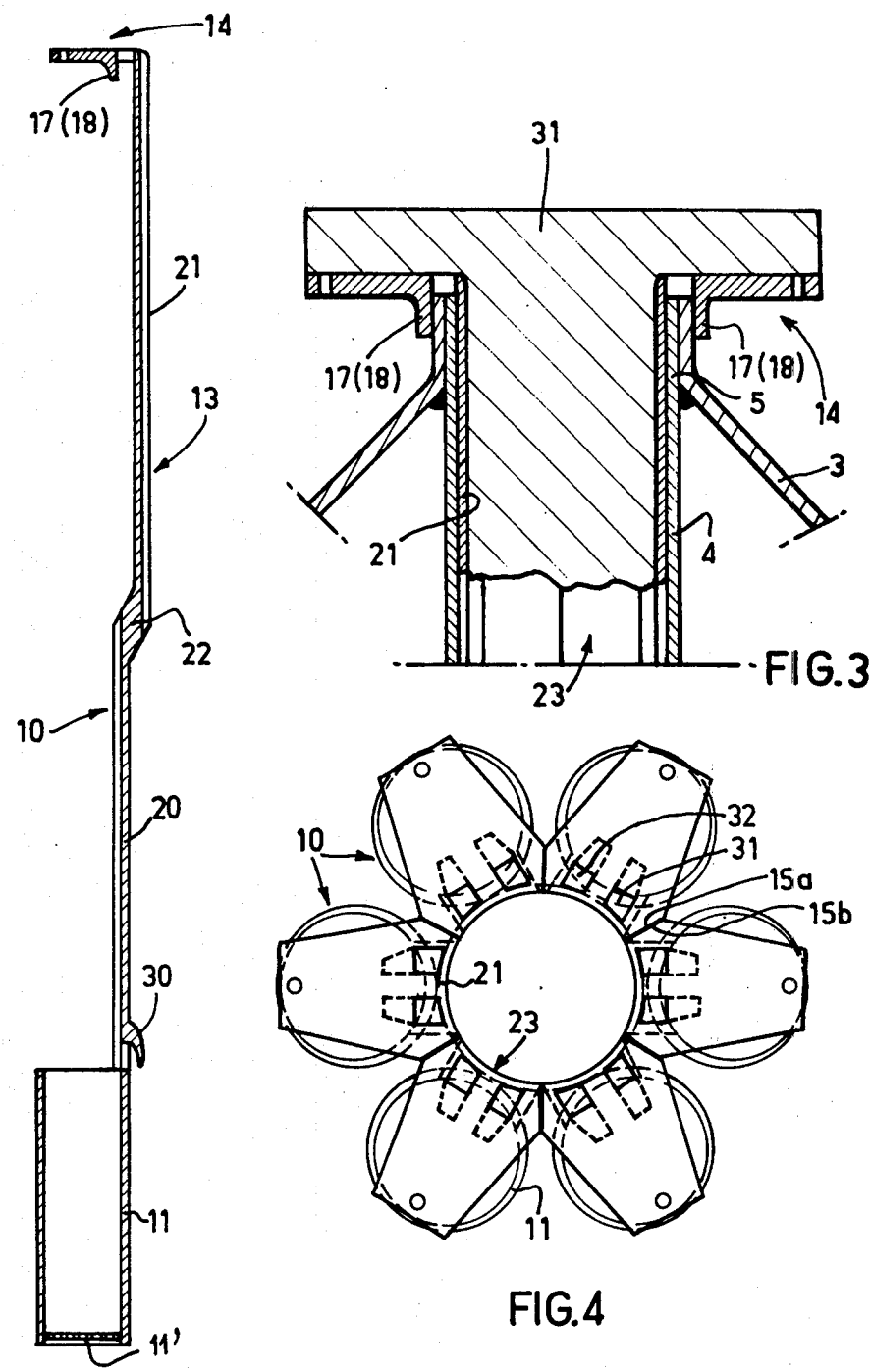

CRYOGENIC STORAGE DEVICES

BACKGROUND OF THE INVENTION

The present invention relates to devices for storing substances such as seeds or semen or the like, of the kind comprising a cryobiological tank having an internal container insulated by a sheath joined to a neck thereof, the upper extremity of said sheath forming a collar, a plurality of carrying cases or canisters for receiving tubular elements receiving the substance to be stored and each associated with location means for locating them and securing them in said tank, incorporating a heat insulated canister rod fitting between said neck and a closure plug and terminating in a retaining head bearing on the said neck collar.

As a rule, the means for locating and securing the carrying cases comprise a double fastening means at a high position on the neck collar or sleeve. To this end, provision is made on the one hand to install in position a tank base divider formed by a plate arranged at right angles to the axis of the neck and comprising rounded notches wherein are engaged circumferentially the carrying cases or canisters accommodating the tubular elements for receiving the material, and on the other hand to install a top divider on the neck rim, which comprises radial notches in the same angular positions as the rounded notches of the bottom plate and wherein is locked a recurved extremity of the securing rod. This arrangement renders it possible to hold the carrying cases in position within the tank whilst the latter is carried, but it will be appreciated that this result is obtained only by the positioning of the particular securing means on the tank and evidently equally of a plug or stopper comprising a barrel provided with longitudinal grooves in which are engaged the extremities of the carrying rods. Furthermore, handling these cases in not very easy since this requires placing them in position simultaneously at the top and bottom, and in particular placing them in position proves to be delicate. A comparatively complex arrangement has also been proposed, for removable fastening of the rod to the canister which, due to an axial offset of the rod and to a removable installation of the same, renders it possible to place the canister on the base of the container in an eccentric position rendering it possible to form a circular row of canisters in contact with the bottom of the container. This arrangement can only be manipulated in a rather unsatisfactory manner and requires excessive care from the operative. It has also been proposed to hang from the rim of the container a canister by means of a partially insulating rod which has a hook intended to reset on the upper edge of the rim, but the system described applies to a single canister only and difficulties would be encountered if several canisters had to be installed in the container in an annular row, in placing these in correct positions, that is to say equidistant ones, so that not only would their manipulation be rather onerous, but also hermeticity at the level of the container plug would be impossible to assure.

It is therefore an object of the invention to provide a device for storage of seed or semen of the type referred to, which is particularly uncomplicated, lightweight and robust in design, and is easy to manipulate.

SUMMARY OF THE INVENTION

In accordance with the invention, these results are obtained in that the rod is secured to the canister in removable manner and in that the top has a circumferential extent along the said rim such that the combined circumferential extent of the tops of a set of canisters co-ordinated with a tank or container corresponds to the available supporting surface situated on the said rim. With this arrangement, an entire operation for placing elements in position in or on the cryobiological container, is eliminated. The result thereof is that the production of the containers is facilitated substantially since the internal container may then be formed by simple stamping and flaring of a single panel of sheet metal.

It is advantageous to produce the canister rod assembly in one piece from a plastics material impervious to low temperatures, and by way of example, reference is made to particular polycarbonates such as "MALROLON" or "LEXAN" or to particular polyamides such as "Polyamide 11," although it will be understood that this list is not restrictive. The rentention tops or heads preferably have identical circumferential extent, which are substantially equal to the circumferential extension of the rim divided by the number of heads. In this manner, all the canisters are interchangeable. In advantageous manner, the suspension rod comprises a flat portion of cylindrical shape capable of being gripped between the inner surface of the rim and a cylindrical plug element.

Due to this system, the assembly of these rods forms a uniform cylindrical sheet at the location of the rim, so that the container plug has a stopper body in the form of a simple cylinder without any groove.

BRIEF DESCRIPTION OF THE DRAWINGS

In order that the invention may be more clearly understood, reference will now be made to the accompanying drawings which show one embodiment thereof by way of example, and in which:

FIG. 2 is an elevation of a carrying case in accordance with the invention, FIG. 3 is an enlarged scale view in vertical cross section at the level of the plug, and FIG. 4 is an enlarged scale plan view prior to insertion of the plug.

DETAILED DESCRIPTION OF PREFERRED EMBODIMENT

Figure 1:
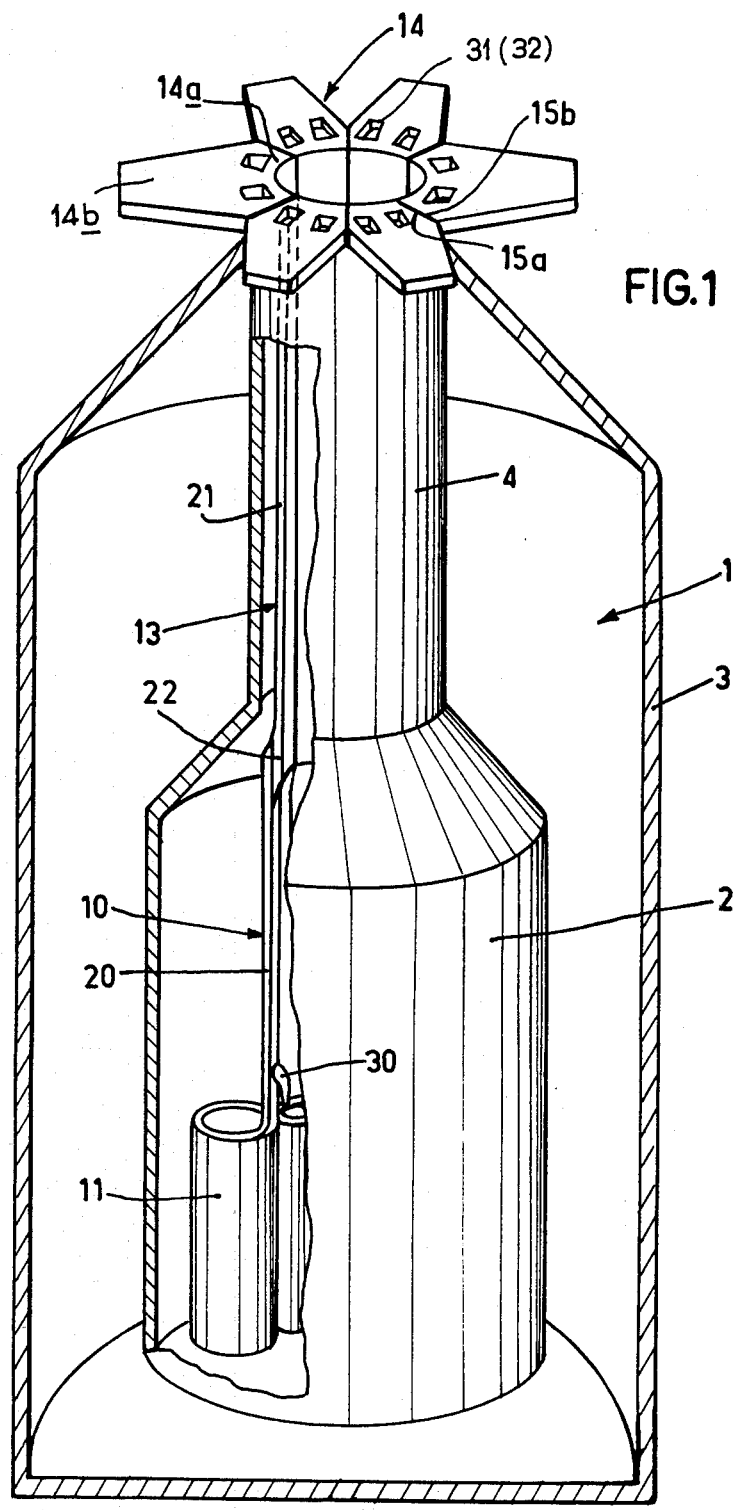
FIG. 1 is a partially cross-sectional view in perspective of a storage device in accordance with the invention.

Referring now to the accompanying drawings, a device for storage of seed or semen comprises a tank 1 intended to receive a cryogenic liquid such as liquid nitrogen and to this end comprises an internal container 2 insulated with mutual spacing by a sheath or casing 3 joined to the tank 1 via a neck 4 terminating externally in a rim 5, the interstitial space between the internal container 2 and the sheath 3 being insulated by vacuum in combination, if appropriate, with insulating filling products in granular form, or with layers of alternately reflective and insulating materials. Each carrying case 10 is formed by a canister 11 for receiving material, the material being placed in sealed tubular elements and this canister 11 having a perforated base 11' is extended by a rod 13 of comparatively flat form terminating in a retaining head 14 which has a radial extension the first part 14a of which, situated close to the rod, has sides 15a and 15b which diverge such that the sides 15a and 15b follow radial directions with respect to the supporting rim 5. This head 14 also includes two locking catches 17 and 18 adapted to bear against the outer surface of the rim 5, thus holding each carrying case 10 in the correct position in the vertical direction. The circumferential extent of the part 14a between the edges 15a and 15b is such that all of these parts 14a placed side by side extend throughout the circumferential extent of the rim 5. Each head 14 has a part 14b remote from the rod 13, in the form of a strip rendering it easy to grasp the head once the plug 31 has been withdrawn.

It will be observed that the rod itself has a lower portion 20 joined to an upper portion 21 via a small bend 22 such that the canister is outwardly displaced a little in the standby position within the container, for the purpose of establishing an adequate axial clearance practically equal to that of the neck 4 for withdrawal of any one of the carrying cases 10. The rod portion 21 extends along a longitudinal distance corresponding to at least that of the body of a closure plug 31 and it has a cylindrical curvature which preferably corresponds to that of the neck, and a circumferential extent which is the same as that of the part 14a of the head 14 at the level of the neck, so that when all the carrying cases are placed in position, the set of rod portions 21 of cylindrical shape forms a cylindrical sheet 23 wherein is inserted the cylindrical insulating plug 31. A retaining pawl or catch 30 is advantageously formed to project on the outer surface of the supporting rod 10 a little above the canister 11, and this catch 30 is arranged to engage in one or the other of the two perforations 31 and 32 made for this purpose in the retaining head 14. In this manner, to withdraw one or more seed or semen holder elements, the strip 14b of a carrying case 10 is grasped to bring the corresponding canister 11 into the axial gap within the annular row of the residual canisters and the carrying case is raised upwards vertically until it reaches the level of the neck 4, into the position in which the catch 30 engages in one of the perforations 31 or 32 of another carrying case.

In this position of utilisation, in which the canister remains within the neck 4, the canister not only continues to be refrigerated by the nitrogen vapours, but it equally forms a plug preventing excessive heat losses.

The invention essentially has as its object the storage of seeds and semen and of other biological and vegetable products.

I claim:

1. In a device for storing material at low temperature, comprising a cryobiological tank having an internal container insulated by a sheath joined to a neck of said internal container, the upper end of said neck forming a rim, a plurality of carrying cases with canisters to accommodate material to be stored at low temperature, each carrying case having a canister rod that extends up from the canister and through said neck and out over said rim and rests on said rim, and a closure plug that fits in said neck to close the tank; the improvement in which each said canister rod has a head that extends radially outwardly and rests on said rim, said heads of said canister rods together covering the supporting area present on said rim.

2. A device as claimed in claim 1, said supporting area extending entirely about the circumference of said rim.

3. A device as claimed in claim 2, in which each said head has an identical circumferential extent about the rim, the extent of each said head about the periphery of the rim being equal to the circumference of the rim divided by the number of heads.

4. A device as claimed in claim 1, the upper part of each said suspension rod in the neck comprising a part cylinder adapted to be gripped between the inner surface of said neck and said plug.

5. A device as claimed in claim 1, and catches on said head that bear against the outer surface of said rim.

6. A device as claimed in claim 1, said suspension rod having adjacent its lower end a catch, said retaining heads having perforations into which a said catch of a raised said carrying case is insertable.

7. A device as claimed in claim 1, in which said rod and said canister are of unitary construction in a plastic material impervious to low temperature.

* * * * *